United States Patent
Powell et al.

(10) Patent No.: US 9,662,140 B2
(45) Date of Patent: May 30, 2017

(54) SURGICAL GUIDANCE TOOL TO FACILITATE DELIVERY OF A NEUROSTIMULATOR INTO A PTERYGOPALATINE FOSSA

(71) Applicant: Autonomic Technologies, Inc., Redwood City, CA (US)

(72) Inventors: Ryan Powell, Sunnyvale, CA (US); Benjamin D. Pless, Atherton, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 971 days.

(21) Appl. No.: 13/923,683

(22) Filed: Jun. 21, 2013

(65) Prior Publication Data

US 2013/0345716 A1    Dec. 26, 2013

Related U.S. Application Data

(60) Provisional application No. 61/662,407, filed on Jun. 21, 2012.

(51) Int. Cl.
*A61B 17/34* (2006.01)
*A61N 1/05* (2006.01)
(Continued)

(52) U.S. Cl.
CPC .......... *A61B 17/3468* (2013.01); *A61B 17/24* (2013.01); *A61B 17/3403* (2013.01);
(Continued)

(58) Field of Classification Search
CPC . A61B 90/16; A61B 17/3403; A61B 17/3468; A61B 2017/3407; A61B 90/11;
(Continued)

(56) References Cited

U.S. PATENT DOCUMENTS

| 5,003,990 A * | 4/1991 | Osypka ................. A61M 25/01 600/585 |
| 2006/0052776 A1* | 3/2006 | Desinger ............ A61B 18/1485 606/50 |

(Continued)

FOREIGN PATENT DOCUMENTS

WO    2008133615 A1    11/2008

OTHER PUBLICATIONS

PCT International Search Report and Written Opinion, mailed Nov. 15, 2013, pp. 1-11.

*Primary Examiner* — Melanie Tyson
*Assistant Examiner* — Rachel S Highland
(74) *Attorney, Agent, or Firm* — Tarolli, Sundheim, Covell & Tummino LLP

(57) ABSTRACT

One aspect of the present disclosure relates to a surgical guidance tool configured to facilitate delivery of a neurostimulator to a target craniofacial region of a subject. The surgical guidance tool can include a main body, a securing mechanism, and an adjustable guide mechanism. The main body can have a distal end, a proximal end, and a longitudinal axis extending between the distal and proximal ends. The securing mechanism can be disposed at the distal end and configured to secure a neurostimulator delivery tool to the main body. The guide mechanism can be configured to temporarily mate with a bodily target location of the subject and facilitate positioning of the neurostimulator delivery tool about the target craniofacial region. The guide member can be slidably attached to the distal end and selectively translatable along the longitudinal axis of the main body.

12 Claims, 8 Drawing Sheets

(51) Int. Cl.
  *A61B 90/16* (2016.01)
  *A61B 17/24* (2006.01)
  *A61N 1/36* (2006.01)

(52) U.S. Cl.
  CPC .............. *A61B 90/16* (2016.02); *A61N 1/05* (2013.01); *A61N 1/0546* (2013.01); *A61B 2017/3407* (2013.01); *A61N 1/3605* (2013.01)

(58) Field of Classification Search
  CPC .......... A61B 90/10; A61B 34/70; A61N 1/05; A61N 1/3605; A61N 1/04; A61N 1/0526; A61N 1/0546; A61N 1/0548; A61M 37/0069
  See application file for complete search history.

(56) References Cited

U.S. PATENT DOCUMENTS

| | | | |
|---|---|---|---|
| 2006/0287677 A1 | 12/2006 | Shalev et al. | |
| 2009/0076521 A1* | 3/2009 | Hansen | A61B 17/3468 606/129 |
| 2009/0112084 A1 | 4/2009 | Piferi et al. | |
| 2009/0182403 A1 | 7/2009 | Glukhovsky | |
| 2009/0281378 A1* | 11/2009 | Banju | A61B 1/00133 600/106 |
| 2012/0071890 A1 | 3/2012 | Taylor et al. | |

* cited by examiner

SURGICAL GUIDANCE TOOL TO FACILITATE DELIVERY OF A NEUROSTIMULATOR INTO A PTERYGOPALATINE FOSSA

RELATED APPLICATION

The present application claims the benefit of U.S. Provisional Patent Application Ser. No. 61/662,407, filed Jun. 21, 2012, which is hereby incorporated by reference in its entirety.

TECHNICAL FIELD

The present disclosure relates generally to surgical tools configured to facilitate delivery of medical devices to a craniofacial region of a subject, and more particularly to surgical guidance tools configured to facilitate delivery of an implantable neurostimulator to a pterygopalatine fossa of a subject.

BACKGROUND

Electrical stimulation of peripheral and central neural structures has shown increased interest due to the potential benefits it may provide to individuals suffering from many neurological and behavioral diseases. Many of these therapies today are not well accepted due to the invasive nature of the therapy, even though the efficacy is quite good. This has created a need for less invasive therapies that are directed toward patient and physician clinical needs.

Headaches are one of the most debilitating ailments that afflict millions of individuals worldwide. The specific pathophysiology of headaches is unknown. Known sources of headache pain consist of trauma, vascular, autoimmune, degenerative, infectious, drug and medication-induced, inflammatory, neoplastic, metabolic-endocrine, iatrogenic, musculoskeletal and myofacial causes. Also, even though the possible underlying cause of the headache pain is identified and treated, the headache pain may persist.

Currently, the sphenopalatine (pterygopalatine) ganglion (SPG) is a target of manipulation in clinical medicine to treat headaches. The SPG is an extracranial neuronal center located behind the nose. It consists of parasympathetic neurons that innervate (in part) the middle cerebral and anterior cerebral blood vessels, the facial blood vessels, and the lacrimal glands. The SPG also consists of sympathetic and sensory nerve fibers that pass through the SPG in route to their end organs. Manipulation of the SPG is mostly performed in attempted treatments of severe headaches, such as cluster headaches or chronic migraines.

Various clinical approaches have been used for over 100 years to modulate the function of the SPG to treat headaches. These procedures vary from least invasive (e.g., transnasal anesthetic blocks) to much more invasive (e.g., surgical ganglionectomy), as well as procedures, such as surgical anesthetic injections, ablations, gamma knife and cryogenic surgery. These later procedures are very invasive, and most are non-reversible. In both cases, the surgical approach is typically through the nostrils or the greater palatine foramen.

SUMMARY

The present disclosure relates generally to surgical tools configured to facilitate delivery of medical devices to a craniofacial region of a subject, and more particularly to surgical guidance tools configured to facilitate delivery of an implantable neurostimulator to a pterygopalatine fossa of a subject.

One aspect of the present disclosure relates to a surgical guidance tool configured to facilitate delivery of a neurostimulator to a target craniofacial region of a subject. The surgical guidance tool can comprise a main body, a securing mechanism, and an adjustable guide mechanism. The main body can have a distal end, a proximal end, and a longitudinal axis extending between the distal and proximal ends. The securing mechanism can be disposed at the distal end and configured to secure a neurostimulator delivery tool to the main body. The guide mechanism can be configured to temporarily mate with a bodily target location of the subject and facilitate positioning of the neurostimulator delivery tool about the target craniofacial region. The guide member can be slidably attached to the distal end and selectively translatable along the longitudinal axis of the main body.

Another aspect of the present disclosure relates to a surgical guidance tool configured to facilitate delivery of a neurostimulator to a target craniofacial region of a subject. The surgical guidance tool can comprise a main body, a securing mechanism, and an adjustable guide mechanism. The main body can have a distal end, a proximal end, and a longitudinal axis extending between the distal and proximal ends. The securing mechanism can be disposed at the distal end and configured to secure a neurostimulator delivery tool to the main body. The guide mechanism can be configured to temporarily mate with a bodily target location of the subject and facilitate positioning of the neurostimulator delivery tool about the target craniofacial region. The guide member can be slidably attached to the distal end and selectively translatable along the longitudinal axis of the main body. The securing member can further include a gimbaled arm member having a distal end adapted to mate with the bodily target location.

Another aspect of the present disclosure relates to a method for delivering a neurostimulator to within close proximity of a sphenopalatine ganglion (SPG) of a subject. One step of the method can include creating a three-dimensional (3D) model of a skull of the subject. A portion of a neurostimulator delivery tool can then be shaped to match the curvature of an implantation pathway to the SPG based on the 3D model. Next, the neurostimulator delivery tool can be secured to a surgical guidance tool. The surgical guidance tool can comprise a main body, a securing mechanism disposed at a distal end of the main body, and an adjustable guide mechanism that is slidably attached to the distal end and selectively translatable along a longitudinal axis of the main body. The neurostimulator delivery tool can be advanced until the surgical guidance tool contacts a bodily target location of the subject and thereby positions a portion of the neurostimulator delivery tool in close proximity to a pterygopalatine fossa of the subject. A neurostimulator can then be delivered in close proximity to the SPG via the neurostimulator delivery tool.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
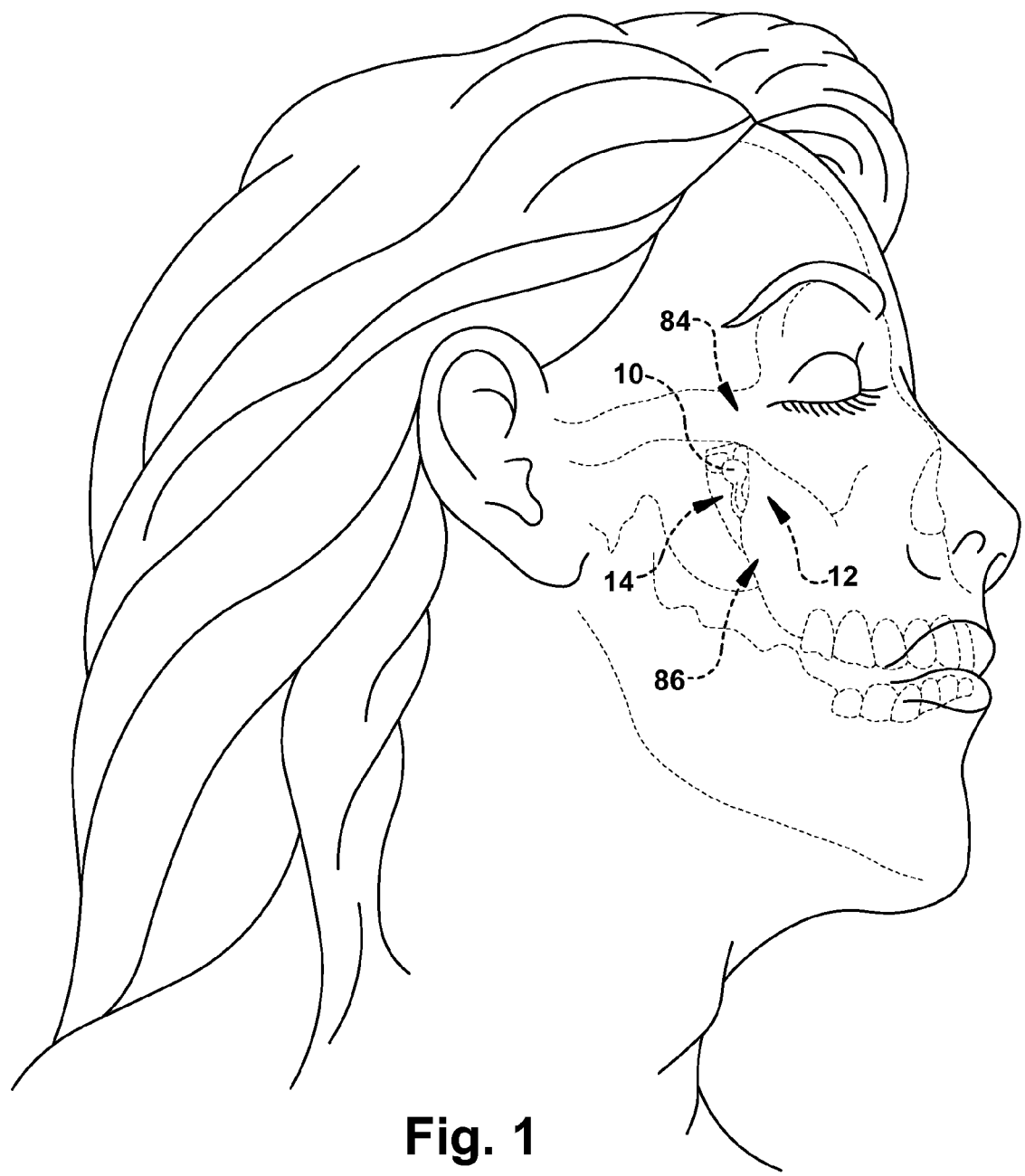
FIG. 1 is a schematic illustration showing the position of a sphenopalatine ganglion (SPG) lying within the pterygopalatine fossa (PPF) of a human subject.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "bodily target location" can include any bony anatomical structure or soft tissue structure that may be used as a guide (e.g., a visual cue) or marker. In some instances, a bodily target location can include one or more fiducial markers. For example, a bodily target location can include a bony anatomical structure having at least one fiducial marker disposed thereon or otherwise associated therewith. Alternatively, a bodily target location can include a fiducial marker located about a surface (e.g., an external surface) of a subject. Examples of bodily target locations are provided below.

As used herein, the term "in communication" can refer to at least a portion of an electrode being adjacent, in the general vicinity, in close proximity, or directly next to and/or directly on (e.g., in physical contact with) a target nerve or nerve structure, such as a sphenopalatine ganglion (SPG), a sphenopalatine nerve (SPN) (also called the "pterygopalatine nerve"), a vidian nerve (VN) (also called "the nerve of the pterygoid canal"), a greater petrosal nerve (GPN), a lesser petrosal nerve, a deep petrosal nerve (DPN), or a branch thereof (e.g., a nasopalatine nerve, a greater palatine nerve, a lesser palatine nerve, or a superior posterior alveolar nerve). In some instances, the term can mean that at least a portion of an electrode is "in communication" with a target nerve or nerve structure if application of a therapy signal (e.g., an electrical signal) thereto results in a modulation of neuronal activity to elicit a desired response, such as modulation of a sensory signal generated in, or transmitted through, the target nerve or nerve structure.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the terms "modulate" or "modulating" with reference to activity of a target nerve or nerve structure can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating"

can also be used to refer to a masking, altering, overriding, or restoring of neuronal activity.

As used herein, the terms "substantially blocked" or "substantially block" when used with reference to activity of a target nerve or nerve structure can refer to a complete (e.g., 100%) or partial inhibition (e.g., less than 100%, such as about 90%, about 80%, about 70%, about 60%, or less than about 50%) of nerve conduction therethrough. For example, the terms "block", "blocking", and "blockade" can refer to the disruption, modulation, and/or inhibition of nerve impulse transmissions through a target nerve or nerve structure.

As used herein, the term "activity" when used with reference to a target nerve or nerve structure can, in some instances, refer to the ability of a nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on a nerve, neuron, or fiber of a target nerve or nerve structure.

As used herein, the terms "prevent" or "preventing" shall have their plain and ordinary meaning to one skilled in the art of pharmaceutical or medical sciences. For example, "prevent" can mean to stop or hinder a medical condition, such as a headache.

As used herein, the terms "suppress" or "suppressing" when used with reference to a medical condition can refer to refer to any quantitatively or qualitatively measurable or observable reduction or attenuation in a medical condition (e.g., a sign or symptom associated with the medical condition).

As used herein, the terms "treat" or "treating" can refer to therapeutically regulating, preventing, improving, alleviating the symptoms of, and/or reducing the effects of a medical condition. As such, treatment also includes situations where a medical condition, or at least symptoms associated therewith, is completely inhibited, e.g., prevented from happening or stopped (e.g., terminated) such that the subject no longer suffers from the medical condition, or at least the symptom(s) that characterize the medical condition.

Overview

A brief discussion of the pertinent neurophysiology is provided to assist the reader with understanding certain aspects of the present disclosure.

The sphenopalatine ganglia 10 (SPG) are located on both sides of the head (FIG. 1). It shall be assumed for the following discussion of the present disclosure that reference is being made to the SPG 10 located on the left side of the head. The SPG 10 is located behind the posterior maxilla 12 in the pterygopalatine fossa (PPF) 14, posterior to the middle nasal turbinate (not shown in detail). The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor). The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 include, but are not limited to, sensations to the upper teeth, feelings of foreign bodies in the throat, and persistent itching of the ear. The SPG 10 transmits sensory information, including pain, to the trigeminal system via the maxillary division and ophthalmic division (not shown).

The present disclosure relates generally to surgical tools configured to facilitate delivery of medical devices to a craniofacial region of a subject, and more particularly to surgical guidance tools configured to facilitate delivery of an implantable neurostimulator to a PPF 14 of a subject. Surgical delivery of medical devices to certain target nerves or nerve structures, such as the SPG 10 is complicated by the surrounding craniofacial anatomy, which is often very tortuous and highly constrained in terms of space for device maneuverability and implantation. Delivery of medical devices to target nerves or nerve structures in the craniofacial region thus requires that such device are carefully advanced to their target sites with highly accurate and precise trajectories. In certain aspects, the present disclosure provides a surgical guidance tool 16 (FIG. 2) to assist in delivering medical devices, such as neurostimulators to a target nerve or nerve structure (e.g., the SPG 10) associated with a target craniofacial region of a subject (e.g., the PPF 14). As discussed in greater detail below, the present disclosure may be employed to assist in preventing, suppressing, or treating a variety of chronic or acute medical conditions, examples of which are disclosed in U.S. patent application Ser. No. 13/470,480 (hereinafter, "the '480 application").

Surgical Guidance Tools

Figure 2:
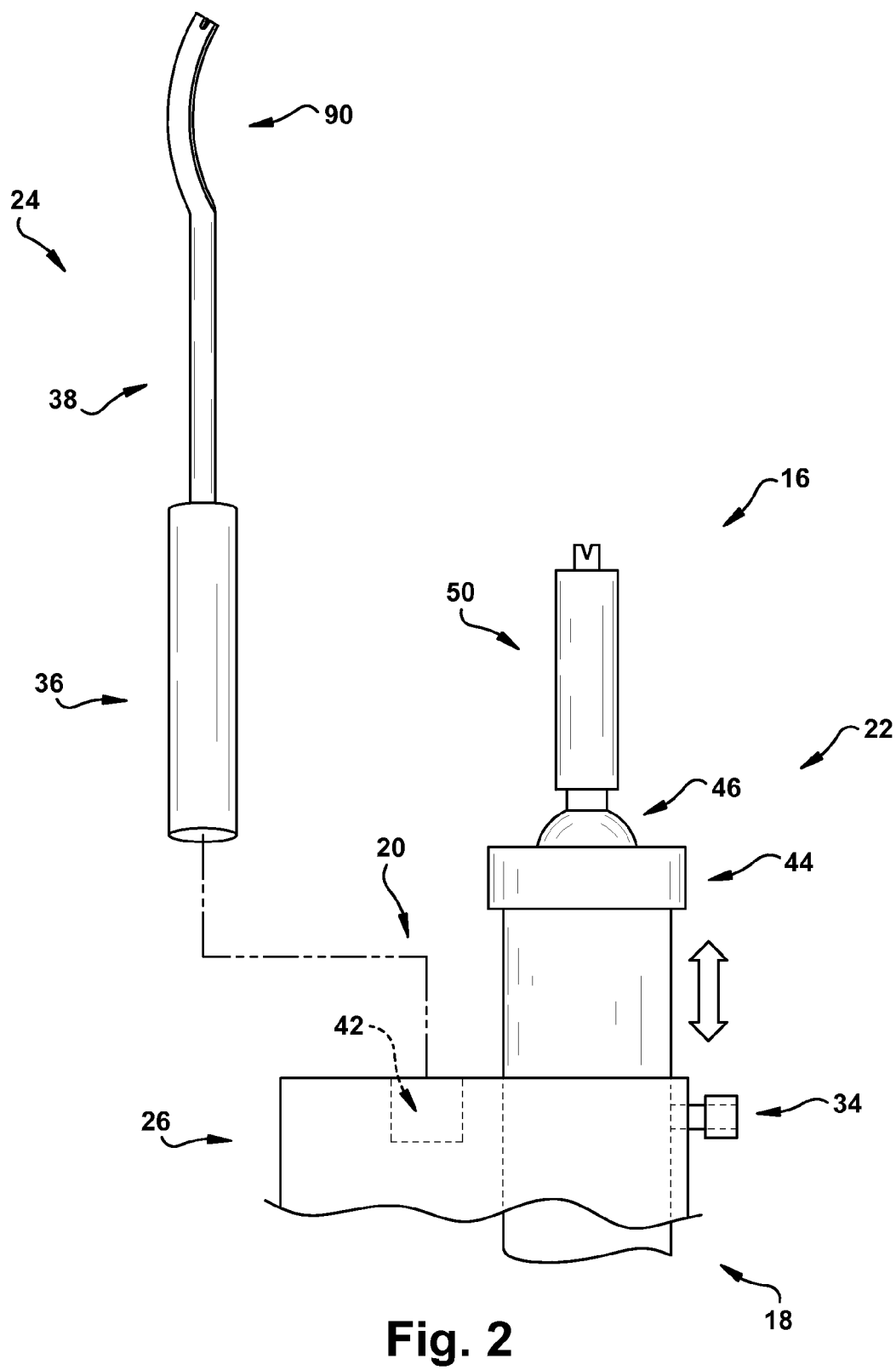
FIG. 2 is a schematic illustration showing a surgical guidance tool configured to facilitate delivery of a neurostimulator to a target craniofacial region of a subject constructed in accordance with one aspect of the present disclosure.

As representative of one aspect of the present disclosure, FIG. 2 shows a surgical guidance tool 16 configured to facilitate delivery of a neurostimulator (not shown) to a target craniofacial region of a subject. The surgical guidance tool 16 can comprise a main body 18, a securing mechanism 20, and an adjustable guide mechanism 22 configured to temporarily mate with a bodily target location of the subject. The securing mechanism 20 can be configured to secure a neurostimulator delivery tool 24 to the main body 18. The guide mechanism 22 can be configured to facilitate positioning of the neurostimulator delivery tool 24 about the target craniofacial region of the subject. As described in more detail below, the surgical guidance tool 16 of the present disclosure provides a simple, ergonomic, and reliable mechanism for guiding a medical device (e.g., a neurostimulator) to target nerve or nerve structure in a precise and accurate manner.

Figure 3A:
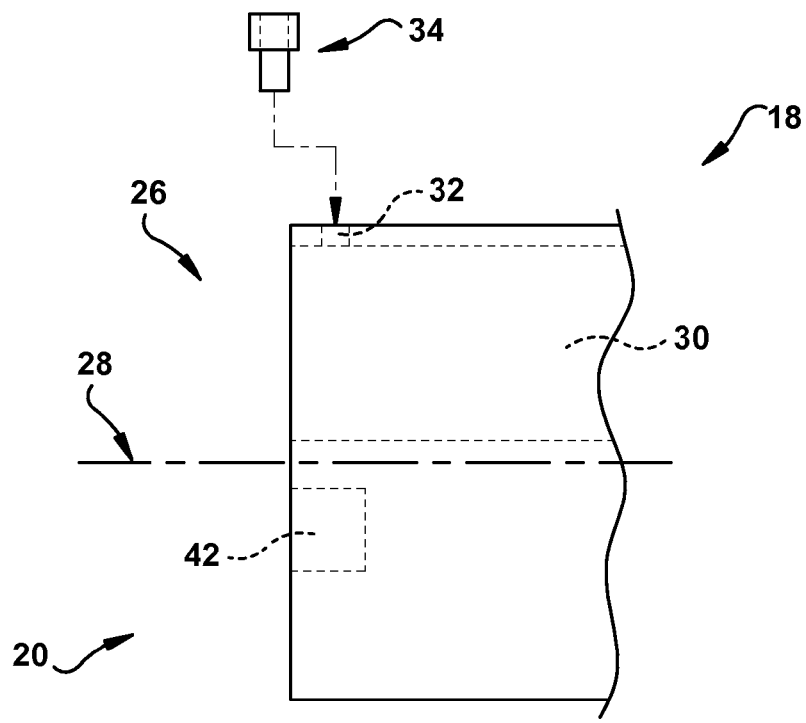
FIG. 3A is a schematic illustration showing a magnified view of a distal end of the surgical guidance tool in FIG. 2.
Figure 3B:
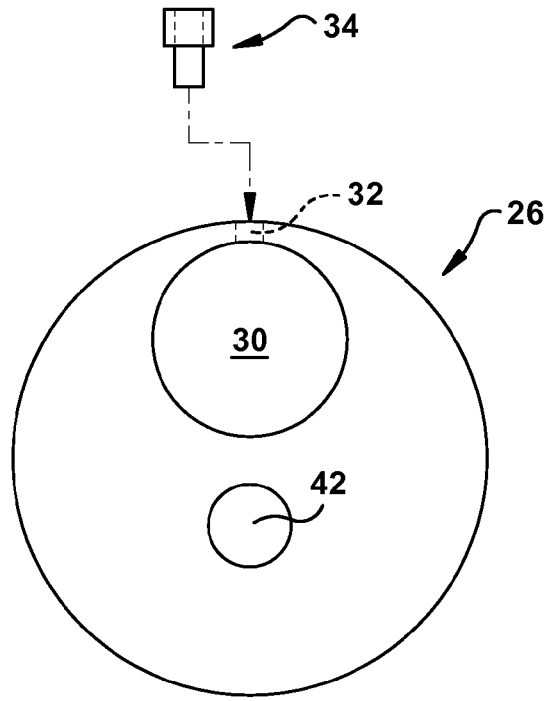
FIG. 3B is a schematic illustration showing a front view of the distal end in FIG. 3A.

In one aspect, the main body 18 of the surgical guidance tool 16 (FIGS. 3A-B) can have a distal end 26, a proximal end (not shown), and a longitudinal axis 28 extending between the distal and proximal ends. The main body 18 can have a generally cylindrical, elongate shape. The main body 18 can have a rigid, semi-rigid or flexible configuration. The main body 18 can have a circular cross-sectional profile as shown in FIG. 3B; however, it will be appreciated that other cross-sectional profiles (e.g., ovoid, square, etc.) are possible. In some instances, the surgical guidance tool 16 (e.g., the main body 18 or the guide mechanism 22) can include one or more fiducial markers (not shown) disposed thereon to facilitate navigation of the surgical guidance tool under image guidance. The main body 18 can be made from one or a combination of medical grade materials, such as titanium or stainless steel, plastics (e.g., PEEK, polycarbonate, nylon) or plastic composites, ceramics (e.g., aluminum, zirconium oxide), glass, combinations of metals, and the like.

Although not shown, the proximal end of the main body 18 can be configured to facilitate tactile or robotic control of the surgical guidance tool 16. To facilitate tactile control, for example, the proximal end can include an ergonomic handle (not shown). The handle can be separately attached to the proximal end or, alternatively, the handle can be formed (e.g., molded) from the same material used to form the main body 18. The handle can include various features to provide grip and tactile maneuverability, such as circumferential ridges or a cross-hatched precut pattern into the material forming the handle. The handle can be made of a rigid or semi-rigid medical grade metal or metal alloy, such as stainless steel, medical grade plastics, polymers, and the like. Examples of robotically-assisted or computer-assisted surgical systems that may be used to aid in surgical procedures involving the surgical guidance tool 16 are known.

The distal end 26 of the main body 18 can include a channel 30 or recessed port that is sized and dimensioned to receive a portion of the guide mechanism 22. The channel 30 can have a circular cross-sectional shape and extend parallel (or substantially parallel) to the longitudinal axis 28 of the main body 18. In some instances, the channel 30 can extend less than the entire length of the main body 18. The channel 30 can have a threaded interior surface, a smooth interior surface, or a combination thereof. As shown in FIGS. 3A-B, the distal end 26 can additionally include at least one secondary channel 32 configured to receive a knob 34 (e.g., a screw). The secondary channel 32 can extend perpendicular (or substantially perpendicular) to the channel 30. In some instances, the secondary channel 32 can be threaded, smooth, or a combination thereof. The secondary channel 32 can be in fluid communication with the channel 30 so that the knob 34 can be inserted into the secondary channel and caused to contact a portion of the guide mechanism 22 disposed in the channel. By adjusting the position of the knob 34 within the secondary channel 32, a user can selectively control translation of the guide mechanism 22 along the longitudinal axis 28 of the main body 18 (indicated by arrow in FIG. 2).

In another aspect, the distal end 26 includes a securing mechanism 20 configured to secure a neurostimulator delivery tool 24 to the surgical guidance tool 16. The neurostimulator delivery tool 24 can include any device or apparatus capable of delivering a neurostimulator to a target craniofacial region. In some instances, a neurostimulator delivery tool 24 can be configured as shown in FIG. 2 and disclosed in the '480 application. For example, the neurostimulator delivery tool 24 can comprise a handle portion 36, an elongate shaft 38 including a contoured distal portion 40, and an insertion groove (not shown) that is sized and dimensioned to receive, support, and guide a neurostimulator deployment apparatus (not shown). In some instances, the securing mechanism 20 can include a port 42 that is recessed within the distal end 26 and configured to receive the handle portion 36 of the neurostimulator delivery tool 24 shown in FIG. 2. In such instances, the port 42 can have a cross-sectional profile (e.g., circular) that is identical (or substantially identical) to the cross-sectional profile of the handle portion 36 of the neurostimulator delivery tool 24. The port 42 can extend parallel (or substantially parallel) to the longitudinal axis 28 of the main body 18.

The port 42 can be configured to securely mate with the neurostimulator delivery tool 24 in a variety of ways including, but not limited to, magnetic, friction fit, screw-in, snap-fit, or a combination thereof. As shown in FIG. 3B, the port 42 can be radially spaced apart from, and vertically aligned with, the channel 30. It will be appreciated, however, that the port 42 can be vertically offset from the channel 30. It will also be appreciated that the securing mechanism 20 need not be disposed within the distal end 26 of the main body 18. In some instances, for example, the securing mechanism 20 can comprise a latch, casing, or housing (not shown) that is located about an exterior surface of the distal end 26 and configured to securely mate with a portion of a neurostimulator delivery tool 24.

Figure 4A:
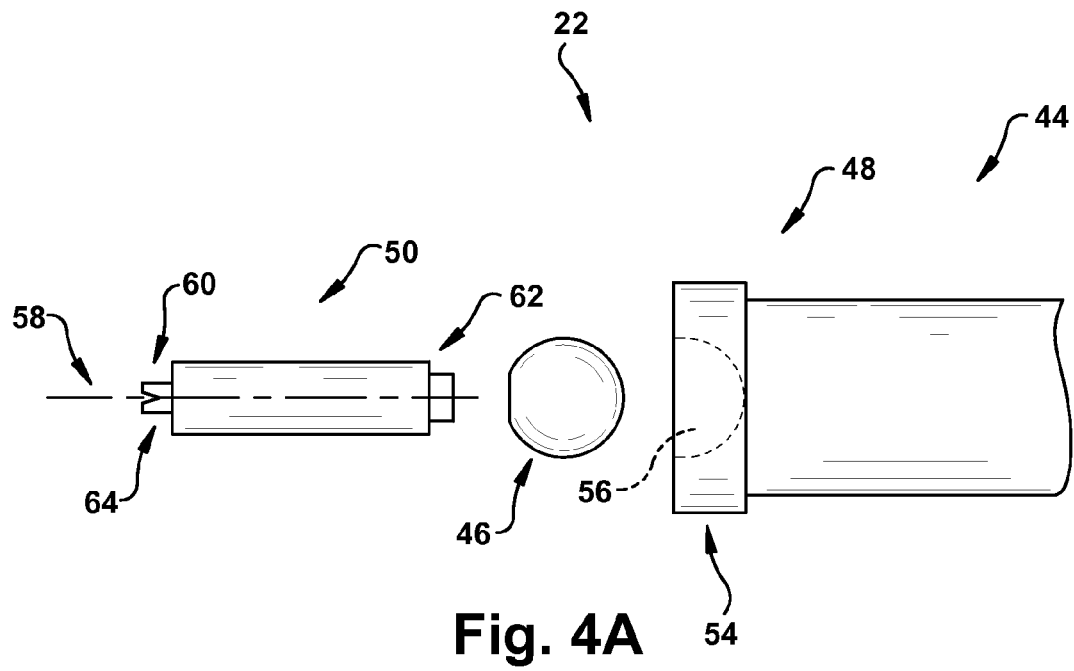
FIG. 4A is a schematic illustration showing an exploded view of a guide mechanism comprising the surgical guidance tool in FIG. 2.

In another aspect, the surgical guidance tool 16 can include an adjustable guide mechanism 22 configured to temporarily mate with a bodily target location of a subject. As shown in FIG. 2, the guide mechanism 22 can be slidably attached to the distal end 26 of the main body 18 and selectively translatable along the longitudinal axis 28 thereof. In some instances, the guide mechanism 22 (FIGS. 4A-B) can comprise an elongate shaft 44, a joint member 46 seated within a distal end 48 of the shaft, and an arm member 50 attached to the joint member. The elongate shaft 44 is configured to be slidably disposed within the channel 30 of the main body 18. The elongate shaft 44 can also include a longitudinal axis 52 extending between the distal end 48 and a proximal end (not shown) thereof. The distal end 48 of the shaft 44 can include a collar portion 54 configured to prevent the shaft from slipping entirely into or within the channel 30. As shown in FIG. 4A, the collar portion 54 can include a bowl-shaped depression 56 configured to receive the joint member 46. The shaft 44 can be made of a rigid medical grade metal or metal alloy, such as stainless steel, medical grade plastics, polymers, and the like.

The joint member 46 is generally spherical or ball-shaped and can be configured similar or identical to a universal joint. The joint member 46 can have a mating surface sized and dimensioned to mate with the bowl-shaped depression 56 of the collar portion 54. The joint member 46 can be securely held within the bowl-shaped depression 56 by one or a combination of retention elements (not show), such as tabs (e.g., located about the collar portion), a series of ball bearings (e.g., disposed within the bowl-shaped depression), magnets, and the like. As discussed in more detail below, the joint member 46 provides a gimbaled platform whereby the arm member 50 of the guide mechanism 22 can be easily rotated to allow contact between the arm member and a bodily target location.

Figure 4B:
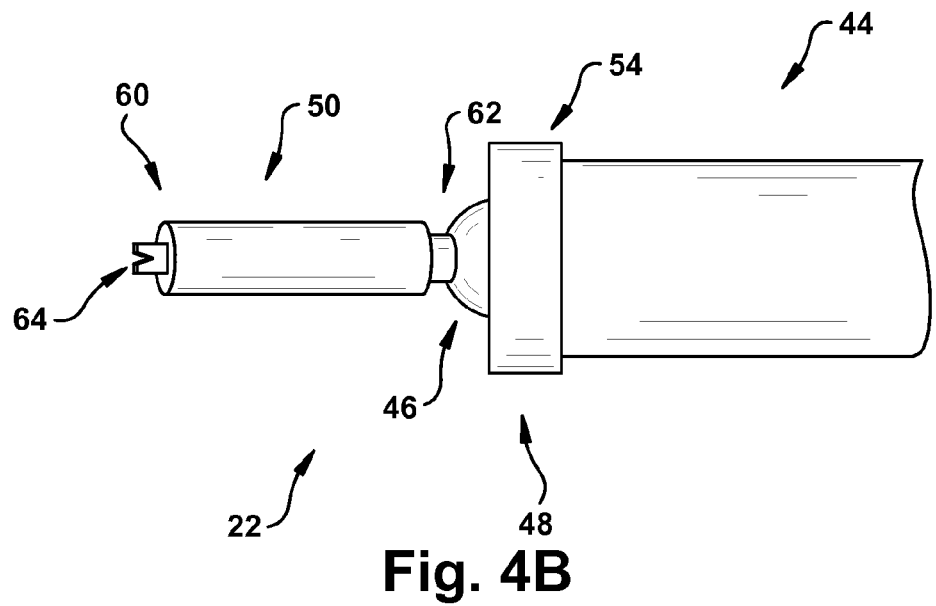
FIG. 4B is a schematic illustration showing an assembled view of the guide mechanism in FIG. 4A.

Referring to FIGS. 4A-B, the arm member 50 can have a cylindrical shape and include a longitudinal axis 58 that extends between a distal end 60 and a proximal end 62 thereof. The arm member 50 can have a rigid, semi-rigid or flexible configuration. The proximal end 62 of the arm member 50 can be adapted to securely mate with the joint member 46. For example, the proximal end 62 of the arm member 50 can include a threaded portion (not shown) adapted to mate with a reciprocal threaded channel (not shown) of the joint member 46. The distal end 60 of the arm member 50 can be configured to securely mate with a bodily target location. In some instances, the distal end 60 of the arm member 50 can include an atraumatic mating element 64 that is shaped and dimensioned to securely mate with the bodily target location. To securely mate with a tip of a tooth, for example, the mating element 64 can have a bifurcated or prong-shaped configuration as shown in FIGS. 4A-B. The mating element 64 can comprise a separate structure that is directly attached to the arm member 50 or, alternatively, the mating element can be an integral part of the arm member (e.g., molded or formed from the same material used to make the arm member). Depending upon the particular target craniofacial region and the selected neurostimulator delivery tool 24, it will be appreciated that the guide mechanism 22 can include two or more arm members 50 or, alternatively, that the distal end 60 of the arm member can have a Y-shaped (or even a trident-shaped) configuration to permit contact between several different bodily target locations and the guide mechanism.

Figure 4C:
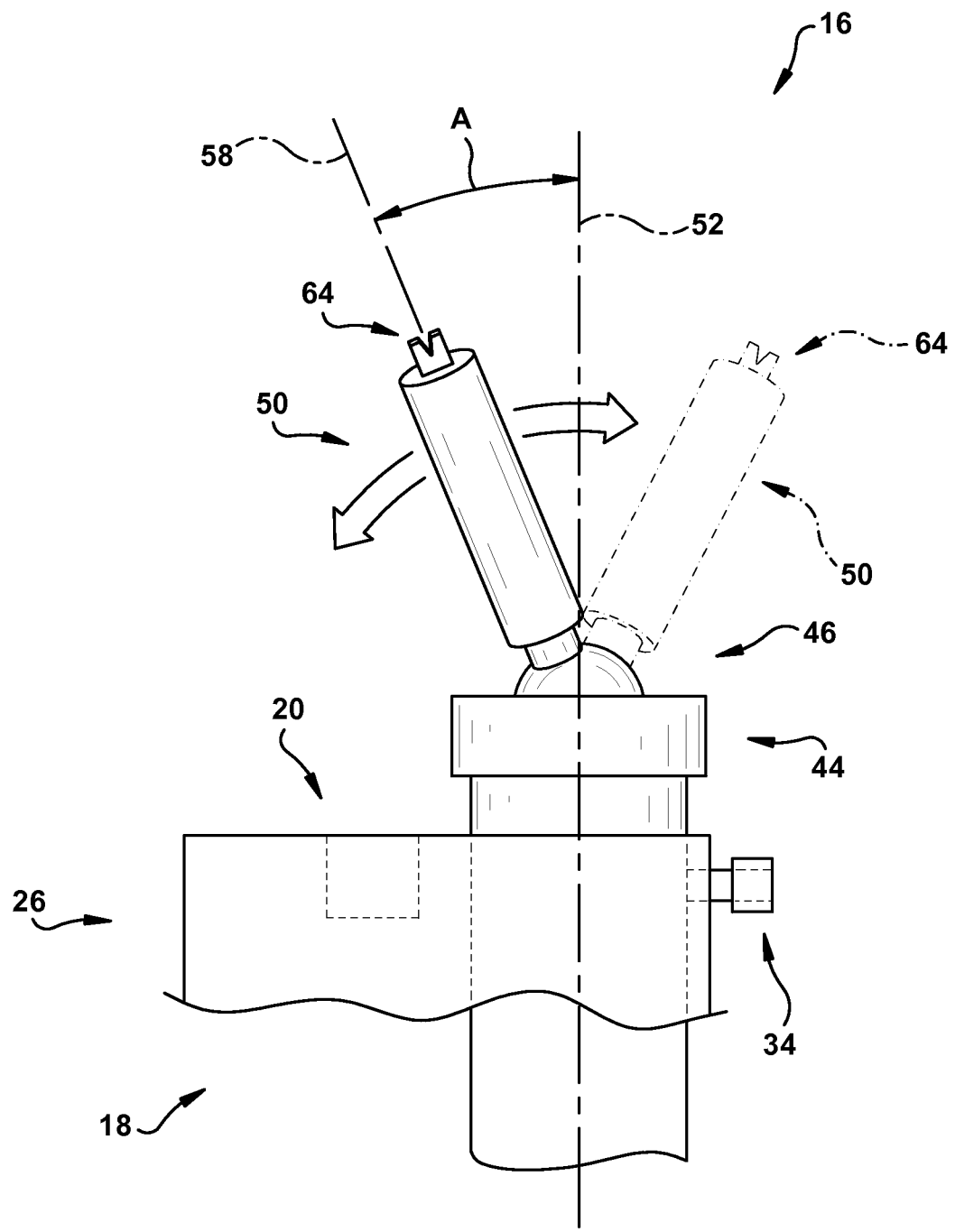
FIG. 4C is a schematic illustration of the surgical guidance tool in FIG. 2 (neurostimulator delivery tool omitted for clarity)
Figure 4D:
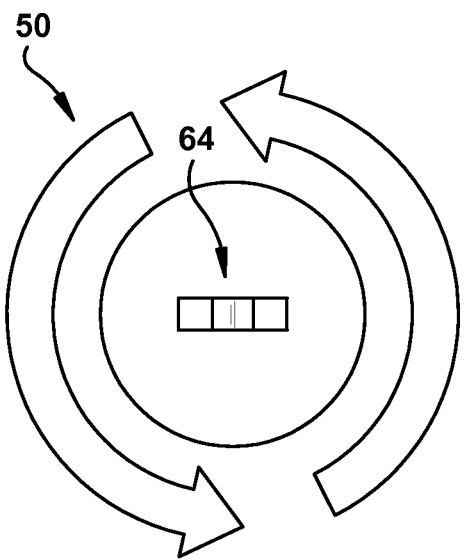
FIG. 4D is a schematic illustration showing the front of an arm member comprising the guide mechanism in FIGS. 4A-B.
Figure 4E:
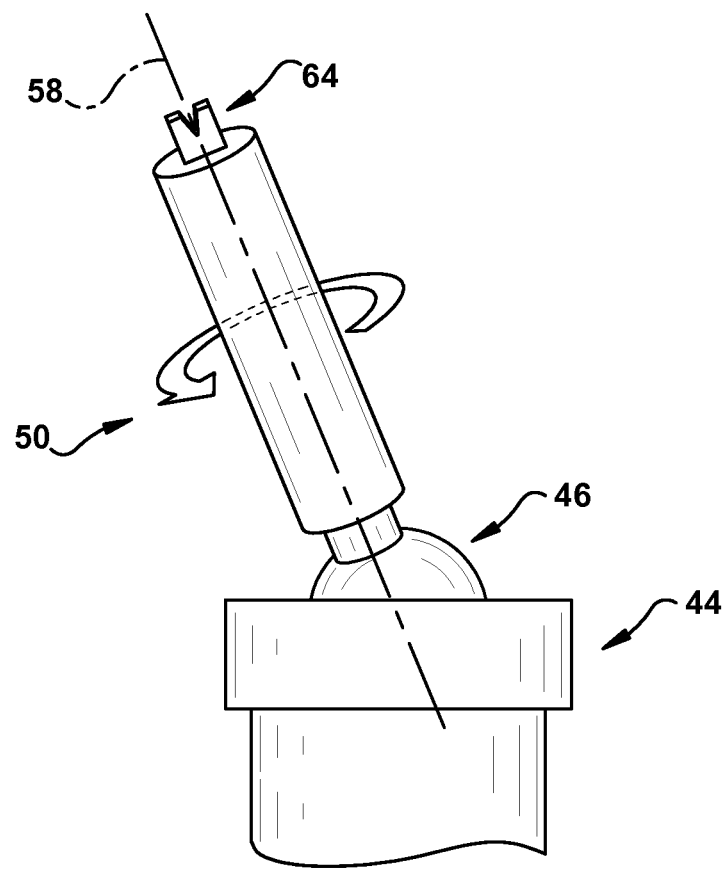
FIG. 4E is a perspective view showing the arm member in FIG. 4D.

FIGS. 4C-E illustrate the gimbaled arm member 50 and the multiple ranges of motion imparted thereto by the joint member 46. As shown in FIG. 4C, for example, the arm member 50 may be movable relative to the shaft 44 so as to form an angle A between the longitudinal axis 58 of the arm member and the longitudinal axis 52 of the shaft. In some instances, the angle A can be varied (e.g., by moving the arm member 50) from about 0° to about 90°. As shown in FIGS. 4D-E, it will be appreciated that the arm member 50 is rotatable 360° relative to the longitudinal axis 58 of the arm member (indicated by arrows). Advantageously, the gimbaled arm member 50 imparts the surgical guidance tool 16 with maximum flexibility to accommodate a variety of different bodily target locations and thereby facilitate accurate and precise advancement of neurostimulator delivery tools 24 to a target craniofacial region.

Methods

Figure 5:
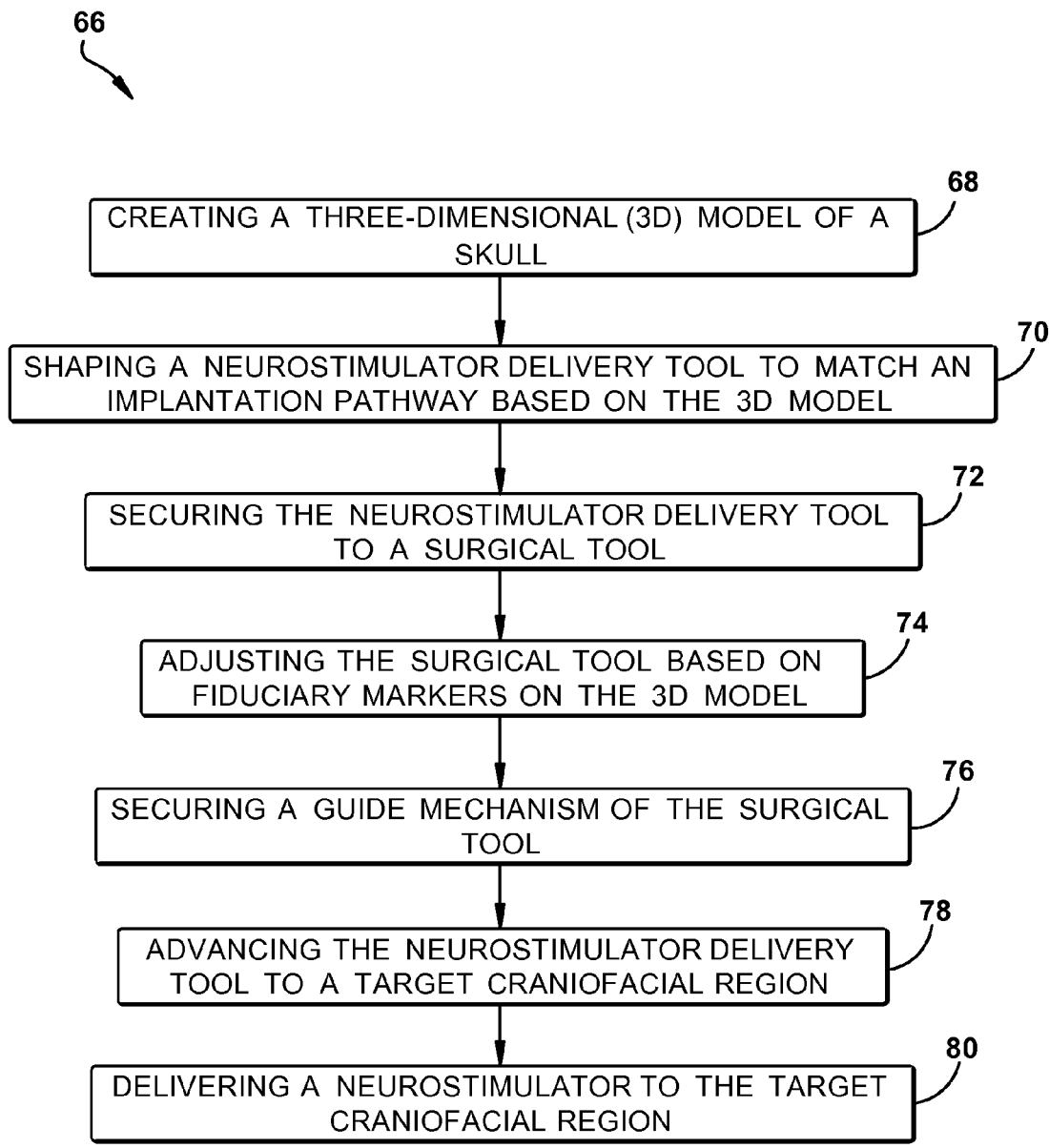
FIG. 5 is a process flow diagram showing a method for delivering a neurostimulator to within close proximity of a SPG of a subject according to another aspect of the present disclosure.

Another aspect of the present disclosure can include a method 66 (FIG. 5) for delivering a neurostimulator to within close proximity of a SPG 10 of a subject. In some instances, the method 66 can include the following steps: creating a three-dimensional model of the skull of the subject; shaping a portion of a neurostimulator delivery tool 24 to match the curvature of an implantation pathway to the SPG 10 based on the 3D model; securing the neurostimulator delivery tool to a surgical guidance tool 16; advancing the neurostimulator delivery tool until the surgical guidance tool contacts a bodily target location of the subject and thereby positions a portion of the neurostimulator delivery tool in close proximity to a pterygopalatine fossa of the subject; and delivering a neurostimulator in close proximity to the SPG via the neurostimulator delivery tool. It will be appreciated that neurostimulators deliverable by the method 66 can generally include any active implantable medical device configured for implantation for a relatively short period of time (e.g., to address acute medical conditions) or a relatively long period of time (e.g., to address chronic medical conditions). Additionally, it will be appreciated that such neurostimulators can include one or more elements used to record or monitor a physiological response of a subject's tissue (e.g., a delivered therapy), as well as one or more other components that interface with the patient's tissue (e.g., therapeutic agent delivery mechanisms, sensors, etc.).

One step of the method 66 can include a surgical planning step (Step 68). In some instances, the surgical planning step can include creating a 3D physical model of the subject's skull using, for example, a computed tomography scan. The 3D model can provide a physician or other medical personnel with an accurate representation of the boney structures comprising the target craniofacial region, such as the anterior maxilla (not shown), posterior maxilla 12, zygomatic bone 84 and PPF 14. The 3D model can also provide a physician or other medical personnel with the anatomical details needed to determine an appropriate implantation pathway (e.g., for the neurostimulator delivery tool 24).

The information obtained from Step 68 can be used shape a portion of a neurostimulator delivery tool 24, for example, to match the curvature of the subject's craniofacial anatomy and ensure that the neurostimulator delivery tool is appropriately configured to facilitate delivery of a neurostimulator in close proximity to the PPF and/or SPG (Step 70). Where the neurostimulator delivery tool 24 is configured similar or identical to the one shown in FIG. 2, for example, the distal portion 40 of the shaft 38 can be shaped and dimensioned as disclosed in the '480 application, i.e., for advancement under a zygomatic bone 84 along a maxillary tuberosity 86 towards the PPF 14. In such instances, the distal portion 40 of the shaft 38 can be designed and configured to be inserted trans-orally and thereby maintain contact with the posterior maxilla 12 to elevate a periosteum off of the posterior maxilla and avoid soft tissue dissection. Also in such instances, a distal tip of the shaft 38 can be sized and dimensioned so that the distal tip can align with the PPF 14 when the neurostimulator delivery tool 24 is introduced into the subject.

At Step 72, the neurostimulator delivery tool 24 can be securely attached to the surgical guidance tool 16 (after properly shaping the neurostimulator delivery tool) via the securing mechanism 20 (as described above). Where a neurostimulator delivery tool 24 like the one shown in FIG. 2 is used, the handle portion 36 of the neurostimulator delivery tool can be inserted into the port 42 comprising the securing mechanism 20 so that the neurostimulator delivery tool is securely attached to the surgical guidance tool 16. If it has not been done so already, one or more fiducial markers can be placed on the subject (e.g., on an external surface). Placement of the fiducial maker(s) will depend upon the location of the particular target craniofacial region and the implantation pathway identified using the 3D model. In one example, one or more fiducial markers can be placed on one or more teeth of the subject's upper jaw.

After securing the neurostimulator delivery tool 24 to the surgical guidance tool 16, the guide mechanism 22 can be adjusted, if needed, based on the 3D model and/or anatomical features perceived by a physician or medical personnel (Step 74). For example, the position of the shaft 44 comprising the guide mechanism 22 relative to the main body 18 of the surgical guidance tool 16 can be adjusted by first manipulating the knob 34 so that the shaft can be freely translated within the channel 30. By moving the shaft 44 in a lateral direction (indicated by arrow in FIG. 2), the position of the arm member 50 relative to the distal end 26 of the main body 18 can be selectively adjusted. Once the shaft 44 has been appropriately positioned, the knob 34 can again be manipulated to secure or lock the shaft in the channel 30 (Step 76). Additionally or optionally, the position of the arm member 50 relative to the main body 18 can be adjusted based, for example, on the 3D model and/or anatomical features perceived by a physician or medical personnel. As discussed above, for example, the arm member 50 can be set at a desired angle A (relative to the main body 18) and/or rotated about the longitudinal axis 28 thereof so that the mating element 64 is appropriately positioned for contact with the bodily target location.

Figure 6:
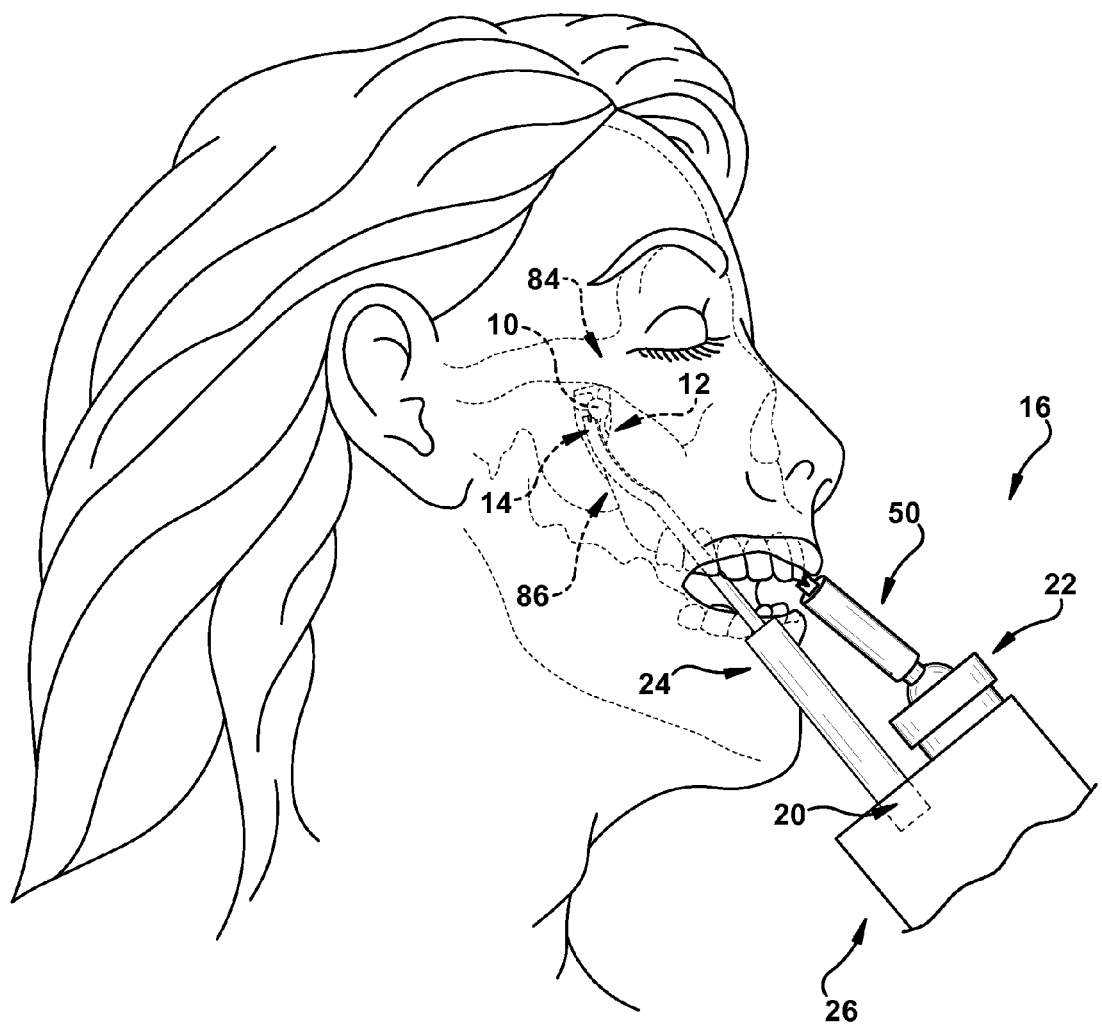
FIG. 6 is a schematic illustration showing the surgical guidance tool in FIG. 2 being used to facilitate placement of a neurostimulator delivery tool about the PPF of a subject.

As shown in FIG. 6, the surgical guidance tool 16 and the neurostimulator delivery tool 24 can then be guided or advanced towards the subject (based on the fiducial marker(s) positioned on the subject) (Step 78). Additionally or alternatively, the surgical guidance tool 16 and the neurostimulator delivery tool 24 can be guided towards the subject based a bodily target location, such as a bony anatomical structure (e.g., the tip of a tooth, such as the tip of a central incisor, a lateral incisor, a canine, or a molar of the subject's upper jaw). In some instances, the surgical guidance tool 16 and the neurostimulator delivery tool 24 can be guided towards the subject by visual or line-of-sight guidance (e.g., without the aid of an imaging modality) to an exposed bodily target location and/or fiducial marker(s). In one example, the neurostimulator delivery tool 24 can be advanced to be in close proximity to the PPF 14. As the distal tip of the neurostimulator delivery tool 24 is moved into close proximity of the PPF 14, the mating element 64 of the guide mechanism 22 contacts the bodily target location, thereby appropriately positioning the distal portion 40 of the neurostimulator deliver tool so that a neurostimulator can be delivered to within close proximity of the SPG 10. A more detailed discussion of implantation procedure for the neurostimulator delivery tool 24 shown in FIG. 2 is provided in the '480 application. Without the use of the surgical guidance tool 16, the physician or surgeon is left with positioning the neurostimulator delivery tool 24 using tactile feedback with or without image-assisted guidance. Using tactile feedback without image-assistance is highly precarious given the tortuous and constricted anterior craniofacial anatomy. And using tactile feedback with image-assistance guidance exposes the subject to unwanted radiation. Advantageously, the surgical guidance tool 16 ensures that a physician or surgeon can accurately and precisely position the neurostimulator delivery tool 24 during a surgical procedure (e.g., without image-assisted guidance) based on the previously determined 3D model.

At Step 80, a neurostimulator can be delivered to the target craniofacial region via the neurostimulator delivery tool 24. In one example, a neurostimulator (not shown) that is similar or identical to the one disclosed in U.S. patent application Ser. No. 13/476,224 (hereinafter, "the '224 application") can be delivered to within close proximity of the SPG 10. For instance, the neurostimulator can include a pulse generator, an integral lead system, and an integral fixation plate. In such instances, the neurostimulator can be delivered to the PPF 14 in an identical or similar fashion as disclosed in the '480 application. Briefly, for example, the neurostimulator can be loaded onto a neurostimulator delivery apparatus (not shown), which is then mated with the neurostimulator delivery tool 24. The neurostimulator delivery apparatus can then be advanced within a predefined groove of the neurostimulation delivery tool 24 into the PPF 14. The neurostimulator can be surgically placed such that the integral lead (with at least one stimulation electrode (not shown)) is located within the PPF 14 directly on or adjacent to the SPG 10 and/or a branch thereof. The integral fixation plate of the neurostimulator can be securely anchored to the zygomatic bone 84. Following fixation of the neurostimulator, the neurostimulator can then be activated so that the stimulation electrode delivers an electrical signal to the SPG 10 and/or a branch thereof to modulate (e.g., substantially block) neural signal transmission therethrough and thereby treat at least one medical condition in the subject.

From the above description of the present disclosure, those skilled in the art will perceive improvements, changes and modifications. For example, it will be appreciated that bodily target locations, such as bony anatomical structures can also include the tip of a tooth (e.g., a central incisor, a lateral incisor, a canine or a molar) of a subject's lower jaw. Such improvements, changes, and modifications are within the skill of those in the art and are intended to be covered by the appended claims. All patents, patent applications, and publication cited herein are incorporated by reference in their entirety.

The following is claimed:

1. A surgical guidance tool configured to facilitate delivery of a neurostimulator to a target craniofacial region of a subject, said surgical guidance tool comprising:
    a main body having a distal end, a proximal end, and a longitudinal axis extending between said distal and proximal ends;
    a securing mechanism disposed at said distal end and being configured to secure a neurostimulator delivery tool to said main body; and
    an adjustable guide mechanism configured to temporarily mate with a bodily target location of the subject and facilitate positioning of the neurostimulator delivery tool about the target craniofacial region, said guide mechanism being slidably attached to said distal end and selectively translatable along said longitudinal axis of said main body, said guide mechanism including a shaft extending from said main body and a gimbaled arm member attached to said shaft by only a single joint member, said gimbaled arm member having a distal end adapted to mate with the bodily target location.

2. The surgical guidance tool of claim 1, wherein said securing mechanism includes a port that is recessed within said distal end and configured to receive the neurostimulator delivery tool.

3. The surgical guidance tool of claim 2, wherein said port is radially spaced apart from said guide mechanism.

4. The surgical guidance tool of claim 1, wherein said guide mechanism further comprises:
    an elongate shaft having a distal end, a proximal end, and a longitudinal axis extending between said distal and proximal ends, said shaft being slidably disposed within a channel of said main body;
    a joint member seated within said distal end of said shaft; and
    an arm member attached to said joint member, said arm member having a longitudinal axis extending between a distal end and a proximal end thereof.

5. The surgical guidance tool of claim 4, wherein the bodily target location is a tip of a tooth.

6. The surgical guidance tool of claim 4, wherein said arm member is rotatable 360° about said longitudinal axis of said arm member.

7. The surgical guidance tool of claim 4, wherein said arm member is movable relative to said shaft so as to form an angle between said longitudinal axis of said arm member and said longitudinal axis of said shaft, said angle being about 0° to about 90°.

8. The surgical guidance tool of claim 4, wherein said distal end of said arm member is configured to securely mate with the bodily target location of the subject.

9. The surgical guidance tool of claim 8, wherein said distal end of said arm member is prong-shaped.

10. The surgical guidance tool of claim 4, wherein said main body further includes a knob for securing said shaft within said channel.

11. The surgical guidance tool of claim 1, wherein said proximal end of said main body is configured to facilitate tactile or robotic control of said surgical guidance tool.

12. The surgical guidance tool of claim 1, wherein the neurostimulation delivery tool further comprises:
    a handle portion;
    an elongate shaft including a contoured distal portion; and
    an insertion groove on the elongate shaft configured to receive, support, and guide a neurostimulator deployment apparatus.

* * * * *